US005509295A

United States Patent [19]
Bartoli

[11] Patent Number: 5,509,295
[45] Date of Patent: Apr. 23, 1996

[54] WEATHER STATION DEVICE

[75] Inventor: Fred J. Bartoli, Schiller Park, Ill.

[73] Assignee: Altronics, a Division of Ridgewood Engineering, Inc., Schiller Park, Ill.

[21] Appl. No.: 307,200

[22] Filed: Sep. 16, 1994

[51] Int. Cl.[6] .................................................. G01N 9/00
[52] U.S. Cl. ........................... 73/30.02; 73/30.04
[58] Field of Search ..................... 73/29.02, 30.01, 73/30.02, 30.04

[56] References Cited

U.S. PATENT DOCUMENTS

| | | | |
|---|---|---|---|
| 3,137,158 | 6/1964 | Krueger | 73/30.01 |
| 3,752,451 | 8/1973 | Kendig | 261/39 B |
| 4,263,804 | 4/1981 | Seemann | 73/30.01 |
| 4,287,762 | 9/1981 | Baer . | |
| 4,375,667 | 3/1983 | Buchan . | |
| 4,403,296 | 9/1983 | Prosky | 364/573 |
| 4,637,261 | 1/1987 | Kraus et al. . | |
| 4,656,864 | 4/1987 | Kraus et al. . | |
| 4,754,651 | 7/1988 | Shortridge et al. . | |
| 4,911,021 | 3/1990 | Shortridge . | |
| 5,019,977 | 5/1991 | LaPointe et al. . | |
| 5,065,704 | 11/1991 | Powell | 123/25 J |
| 5,117,359 | 5/1992 | Eccles . | |
| 5,189,990 | 3/1993 | Powell | 123/25 J |
| 5,255,556 | 10/1993 | Lobdell . | |

*Primary Examiner*—Richard Chilcot
*Assistant Examiner*—Eric S. McCall
*Attorney, Agent, or Firm*—Leydig, Voit & Mayer, Ltd.

[57] ABSTRACT

This invention describes a density altitude measuring device whereby the density altitude is calculated based on atmospheric inputs. The computer of the density altitude measuring device is connected to temperature, pressure and humidity sensors. The sensors send input to the computer describing the ambient atmosphere. The computer then takes sufficient samples from the sensors and calculates the density altitude. Finally, the data is displayed on a screen, storage device, or printer.

8 Claims, 5 Drawing Sheets

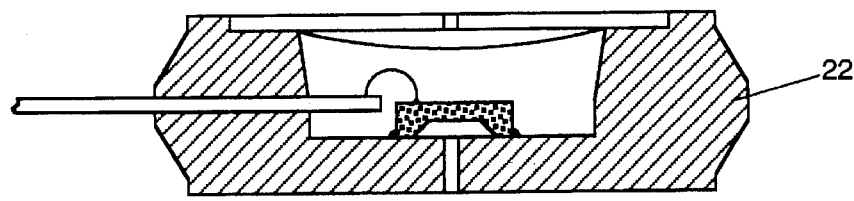
FIG. 5
| | E.T. (SECONDS) | DENSITY ALT. (FEET) |
|---|---|---|
| 1 | 10.006 | 111 |
| 2 | 10.201 | 2440 |
| 3 | 10.00 | 100 |
| 4 | 10.302 | 5071 |
| 5 | 10.183 | 2100 |
| 6 | 10.065 | 612 |
| 7 | 10.262 | 3607 |
| 8 | 10.100 | 902 |
| 9 | 10.152 | 1601 |
| 10 | 10.030 | 403 |
| 11 | 10.30 | 2149 |
| 12 | 10.005 | 110 |
| 13 | 10.208 | 2513 |
| 14 | 10.234 | 2700 |
| 15 | 10.256 | 3483 |
| 16 | 10.261 | 3590 |
| 17 | 10.068 | 800 |
| 18 | 10.292 | 4523 |
| 19 | 10.278 | 4209 |
| 20 | 10.011 | 220 |
FIG. 6
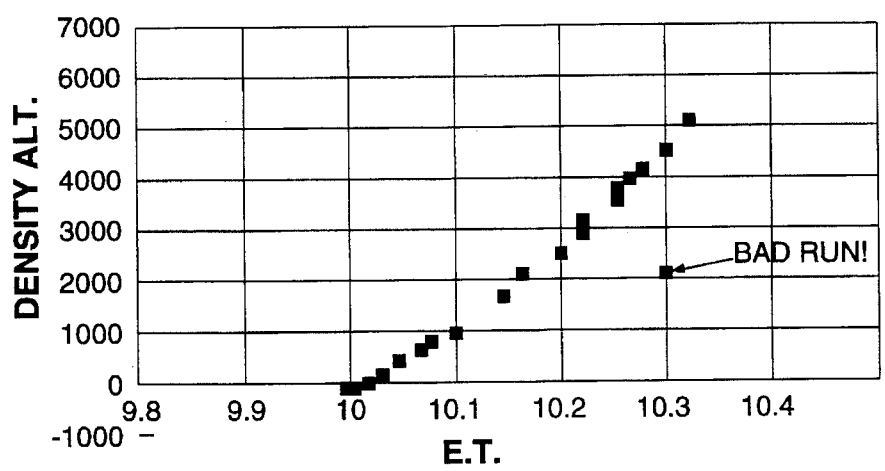
FIG. 7

WEATHER STATION DEVICE

TECHNICAL FIELD

The invention relates to the calculation of the density altitude by monitoring the temperature, pressure and humidity of the atmosphere.

BACKGROUND OF THE INVENTION

In the field of auto racing, there are several methods in which to predict the performance of a race car. One method uses horsepower correction factors. However, this method does not take into consideration different engine sizes, engine combinations, carburetion, or body styles a race car can have, thereby failing as a performance indicator. Since every car is unique and will react in its own way to changes in the atmosphere, one must develop a method to relate the atmosphere to the car's performance.

The key variable in determining the effect of the atmosphere on the car's performance is the amount of oxygen present in the atmosphere. However, the oxygen content is not directly measured. Rather, the density altitude, which indicates the density of the gas elements in the atmosphere, is measured as an index of the car's performance. Oxygen, as one of the gas elements in the atmosphere, is estimated based on the average breakdown of the various gas elements in the atmosphere. Oxygen's percent of concentration is assumed constant in relation to these other gases. Therefore, as the density of the gas changes in the atmosphere, the density of the oxygen also changes in relative proportion.

In order to characterize fully the effect of the atmosphere on the automobile's performance, multiple calculations of different density altitude values are required. One must then plot the natural curve of the car's performance based on the density altitude versus the engine performance. Thus, using statistical regression analysis, a driver can predict the performance of the car based on the plot of the density altitude values.

However, for the density altitude plot to be an effective indicator of the car's performance, it must be particularly accurate. Small changes in density altitude or inaccurate measurements can be the difference between winning and losing in auto racing. As little as a 100 foot change in density altitude can noticeably change the performance of an automobile. In fact, most racers do not realize that a minor change in the atmosphere can equate to a major change in density altitude. On average, a 1° change in temperature, a 0.1 inHg change in pressure, or a 10% change in humidity can cause more than a 100 foot change in density altitude.

Instruments being used in other weather stations have variables that make it impossible to measure density altitude at a level needed to predict the performance of a race car. These inaccuracies can stem from a person's inability to correctly distinguish what the instrument is reading or to correctly calculate the density altitude.

Further, inaccuracies may come from the effect temperature has on the instrument. For example, a change in temperature can have an effect on a barometer or a hydrometer. A barometer is factory calibrated at 70 degrees. Then it is exposed to the heat of 90 degrees, but with the same pressure. The components that make up this barometer can expand or contract causing an error in the reading. Temperature compensated barometers are available, but they are costly. The effects on a hydrometer are similar.

Finally, inaccuracies can come from the instruments lack of accuracy or repeatability. For example, a sling psychrometer's accuracy depends on how fast and how long one slings it, the pressure to which it is exposed, and the contamination of the wick. The reading from a sling psychrometer will differ when taken on two days of the same humidity, but different pressures. Thus, when using standard weather instruments (digital or mechanical), one would be lucky to compute density altitude to plus or minus a few hundred feet. This amount of error in density altitude calculation is too great to be a reliable indicator of automobile performance and is therefore not acceptable.

SUMMARY OF THE INVENTION

It is a general object of the invention to provide a more reliable means to predict a racing automobile's performance based on changes in the atmosphere.

It is a related object of the invention to provide an inexpensive, accurate method in which to measure density altitude.

It is a further related object of the invention to provide a weather station which can repeatedly measure density altitude accurately.

The present invention accomplishes these objectives and overcomes the drawbacks of the prior art by providing a density altitude mechanism which more effectively predicts the performance of a racing automobile. In the present invention, the density altitude mechanism is divided into two separate devices: (1) the sensing device; and (2) the processing device.

The sensing device monitors the temperature, pressure, and humidity of the atmosphere through state of the art sensors. The sensors provide the values by which the processing device can calculate the density altitude.

The processing device receives the information and transmits it to a computer. The computer then calculates the density altitude, increasing accuracy and reliability in two ways. First, the computer polls each of the sensors several times and then averages the values. This enables the computer to minimize aberrant values of pressure, temperature and humidity which an operator may misread. Further, this polling increases consistency from reading to reading of the sensors. Second, the computer uses scientific equations to calculate the density altitude. The computer therefore removes operator error in using the scientific equations to calculate density altitude.

These and other features and advantages of the invention will be more readily apparent upon reading the following description of the preferred embodiment of the invention and upon reference to the accompanying drawings wherein:

BRIEF DESCRIPTION OF THE DRAWINGS

FIG. 5 is a drawing of the pressure sensor used in the density altitude device;

FIG. 6 is a table of density altitude data for a car; and

FIG. 7 is the plot of the density altitude data.

DESCRIPTION OF A PREFERRED EMBODIMENT

Figure 1:
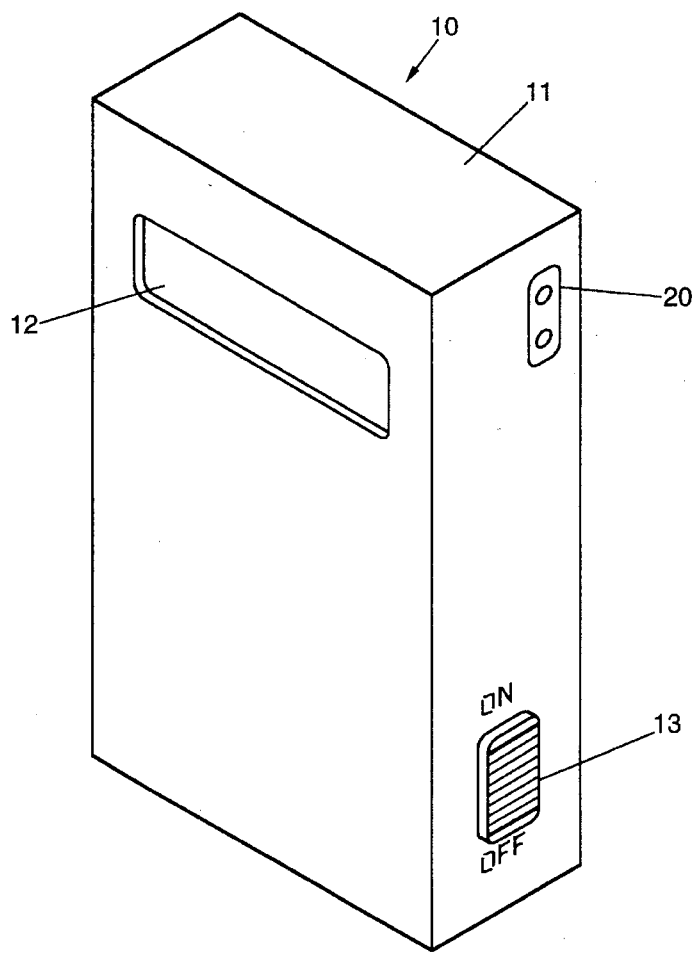
FIG. 1 is a three-dimensional representation of the density altitude device.

Referring to the drawings, there is shown in FIG. 1 an illustrative computer device 10 in a housing 11, having a display 12 and an on-off switch 13. The housing contains a computer 13, a pressure sensor 22, a temperature sensor 23, a humidity sensor 24.

Figure 2:
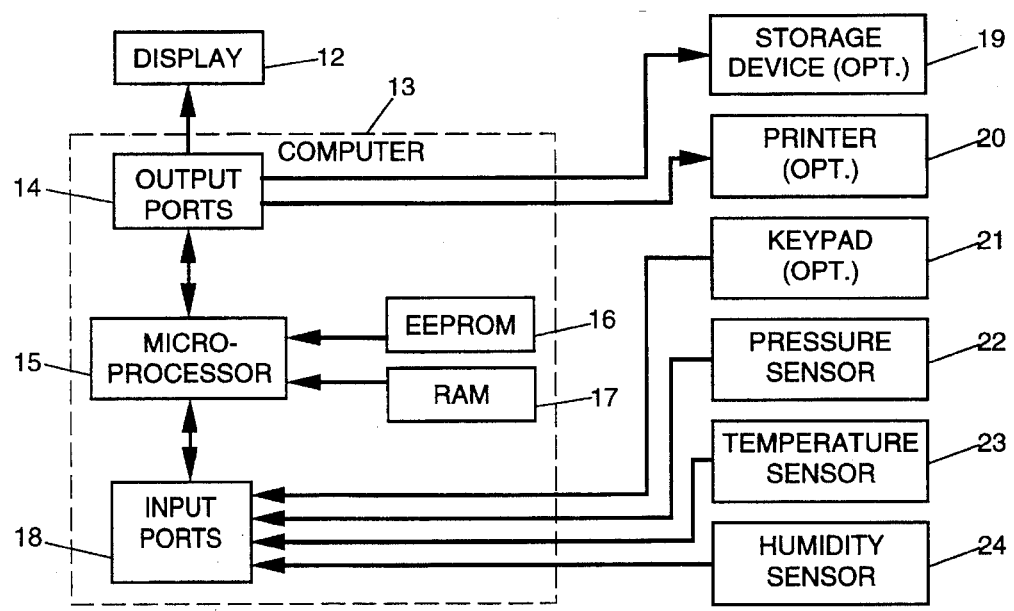
FIG. 2 is a block diagram of the density altitude device according to the invention.
Figure 3:
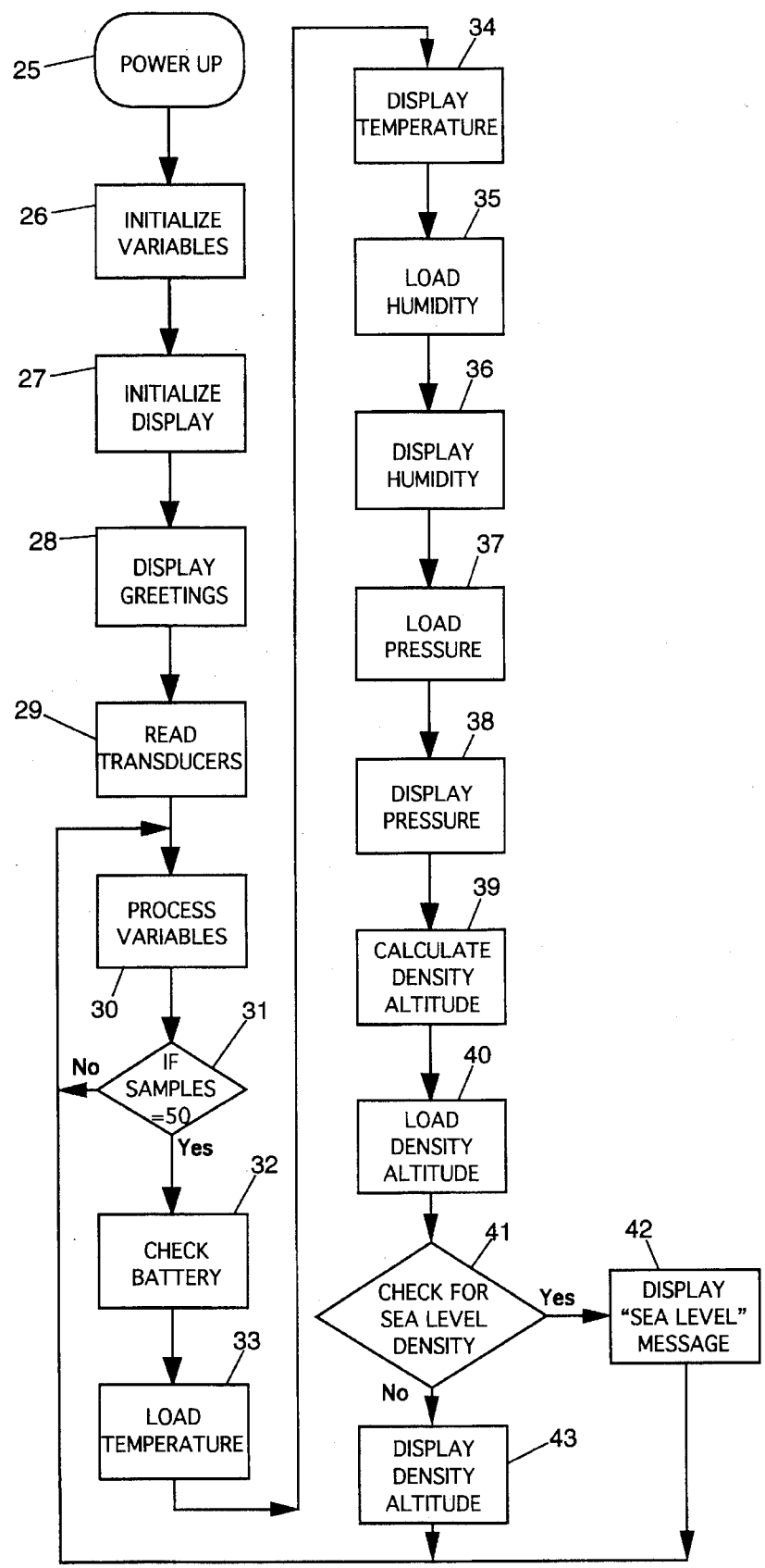
FIG. 3 is a flow chart of the microprocessor operations of the density altitude device.

As shown in FIGS. 2, 3 and 4 conjointly, the computer 13 initializes the density altitude device upon power up 25 by initializing variables 26 which are needed for the density altitude calculation, by initializing the display 27, and by displaying greetings 28. The computer then enters the main loop which calculates the density altitude.

The computer 13 receives sensory input from each of the sensors by reading the transducers 29. The pressure sensor 22 is commercially available and schematically illustrated in FIG. 5. The temperature sensor 23 is a YSI 44004 Precision Thermistor made by YSI Incorporated of Yellow Springs, Ohio. The humidity sensor 24 is a MiniCap 2 Relative Humidity Sensor from Panametrics. Each of the sensors sends input to the input ports 18 of the computer 13.

Figure 4A:
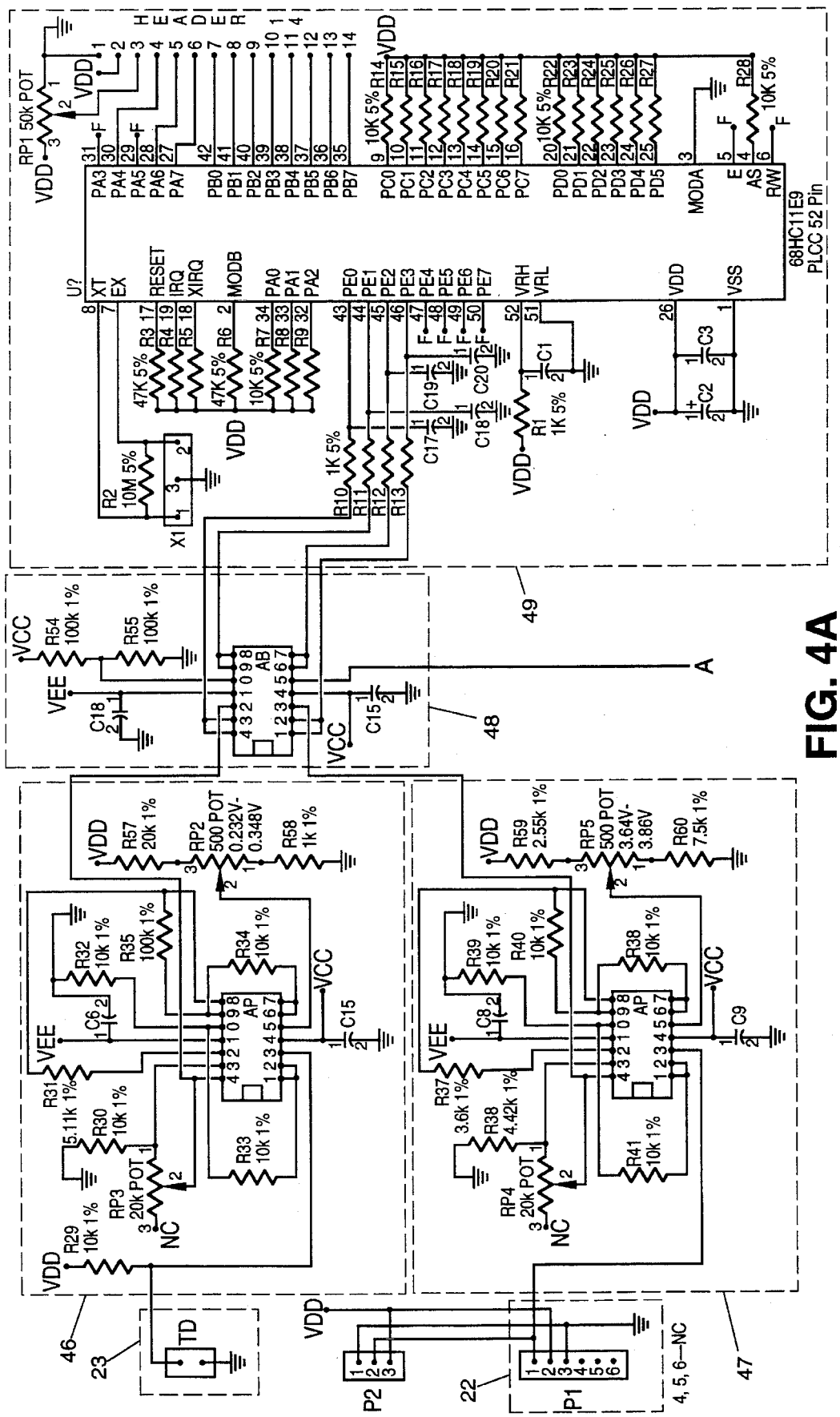
FIGS. 4A and 4B is a circuit diagram of the density altitude device.
Figure 4B:
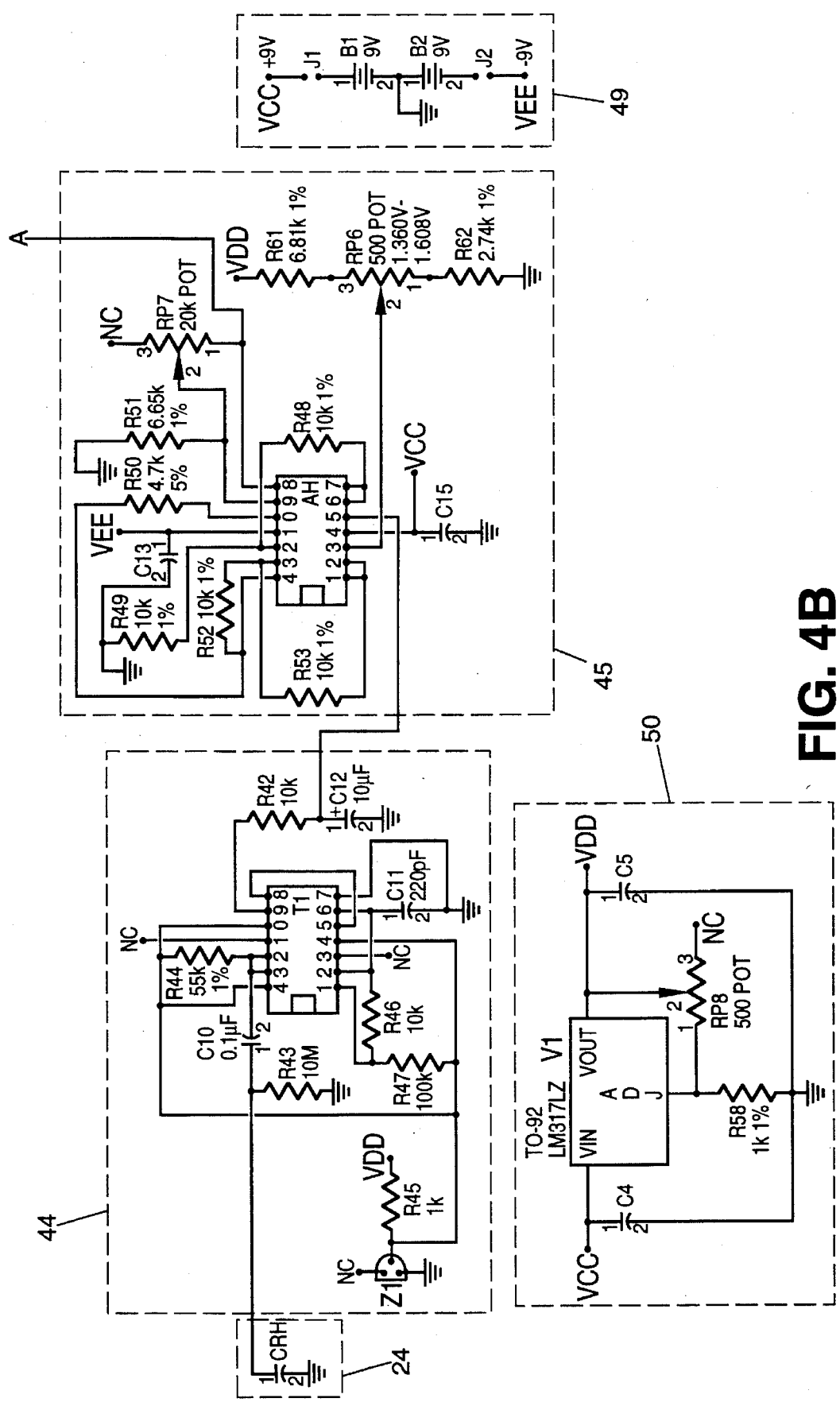

The input ports 18 are a combination of signal conditioners and analog to digital converters, so that the analog input of the sensors can be digitized for a microprocessor 15 to use. As shown in FIGS. 4A and 4B, the humidity sensor 24 requires a humidity pulse width generator and voltage reference 44 to drive the humidity sensor 24. The humidity pulse width generator and voltage reference 44 sends the humidity sensor input to the humidity signal conditioner 45 which then sends the analog voltage to the analog/digital converter 48. The temperature sensor 23 sends its input to a temperature sensor conditioner 46 and then to an analog/digital converter 48. The pressure sensor 22 sends its input also to a pressure sensor conditioner 47 and then to an analog/digital converter 48. The microprocessor 15 accepts the digital inputs from the analog/digital converter 48 and processes the variables 30 by putting them into decimal form. It should be noted that a keypad 21 may also be provided to input values to control the display 12. Said keypad will allow entering and storing in the computer density readings along with corresponding performance variables. Through a statistical regression analysis the computer will then be able to determine the value of a performance variable for a realtime reading of the density altitude. Also, an optional storage device 19 or a printer 20 may be incorporated within or connected to the device.

Next, the microprocessor 15 determines whether there have been enough samples from each of the sensors to calculate an average value of each of the inputs. If the samples are less than fifty 31, then the sensors are read again. This operation of multiple polling of the sensors is to minimize the effect of an aberrant reading from any of the sensors.

If sufficient samples were taken, the density altitude is calculated. The battery is first checked 32 to determine if the battery is low. The density altitude device uses a battery and is therefore capable of portability. As shown in FIG. 4, the battery 50 provides the reference voltages 49. Next the microprocessor 15 loads the temperature 33 and displays the temperature 34, loads the humidity 35 and displays the humidity 36, and loads the pressure 37 and displays the pressure 38.

The microprocessor then calculates the density altitude based on scientific equations. The density altitude value is derived from the ideal gas laws using temperature, relative humidity, and barometric pressure parameters of the atmosphere. The following is an example using parameter values selected at random to show the density altitude algorithm:

Temperature: 70° Fahrenheit.
  In Kelvin: T=294.36 K
Relative Humidity: 50%
  Uw=50
Barometric pressure: 29 inHg
  In Millibars: mb=100 Pa
  p=999.02 mb
Saturation vapor pressure at 70° F.
  es=6.11 * 10 * 7.5 * (T–273)/(237.3+T–273)*100
  es=25.28 mb
Vapor pressure:
  e=Uw * es/100
  e=12.64 mb
Mixing ratio:
  mr=0.62 * e/(p–e)
  mr=0.0080
Virtual temperature:
  Mean molar mass of dry air: Md=28.97
  Mean molar mass of water vapor: Mv=18.02
  Mean molar mass of moist air: Mm=(r+1)/[r/Mv+1/Md]
  Mm=28.83
  Tv=T * Md/ Mm
  Tv=295.68
Density of air without moisture
  Universal Gas Constant: R=8.31
  r1=(Md*p)/R*T*1000)
  r1=1.18 kg/m$^3$
Density of moist air at the virtual temperature:
  r2=(Mm*p)/(R*T,1000)
  r2=1.18 kg/m$^3$
Density of vapor:
  r3=mr * r1
  r3=0.0094 kg/m$^3$
Density of the gas:
  r=r2–r3
  r=1.17 kg/m$^3$
Conversion of the gas density to the Density Altitude in Reference to the US Standard Atmosphere Table
Gas_density_ratio=r/1.225
Density_altitude=log(Gas_density_ratio)/log(0.99997)
Density_altitude=1.597 * 10$^3$ feet For increased accuracy of calculating the density altitude value, the microprocessor can compute several density altitude values, average those values, and display an average density altitude value . Similar to multiple polling of the sensors to increase reliablity of the sensor data, multiple calculations of density altitude increases reliability of the calculated value.

After the density altitude is calculated, the microprocessor checks if the device is at sea level 41. If so, a "sea level" message is displayed 42 using the output ports 14. Otherwise, the calculated density altitude is displayed 43. The display 12 can be a liquid crystal display (LCD).

The density altitude may also be output to a printer 20, which can be hard wired to the computer 13 or be connected to the computer 13 by an infrared connection. Further, the density altitude may be output to a storage device 19, such as a disk drive. When sending the density altitude to the printer 20 or storage device 19, the computer can write a date and time stamp which corresponds to the time in which the temperature, pressure, humidity and density altitude values were calculated. This eases future reference of the calculated values of the computer 13.

After several density altitude values are calculated, they can be listed in a table as shown in FIG. 6. In order to characterize fully the effect of the atmosphere on the car's performance, the calculated density altitude values should be plotted as shown in FIG. 7. Please note that actual graphs can allow one easily to mark density altitude in increments of 10 feet and E.T. in increments of 0.001 seconds. Once the data has been plotted, it becomes easy to tell where a bad run occurred. When using a calculator, one may not have discovered that run #11 was bad and may have entered it into the calculator. The calculator would then incorporate the bad data, thereby corrupting the plot. The hand plot avoids this pitfall.

Once the curve is established, it becomes even simpler to take the present density altitude reading and quickly look up what corresponding E.T. the car should run. The same chart can be used from track to track. To do this, one must measure the density altitude at the new track and make a run. The difference between what the chart predicts and what the car actually runs, ideally, should be the effect of the new track. For instance, at a new track, the density altitude is 2000 feet and the chart predicts the car should run a 10.17, but the car only runs 10.22. The difference can be accounted for in the track being 0.05 seconds slower because of a slight uphill grade. This 0.05 difference can be carried out when trying to predict your next run after the density altitude has changed. This same approach can be used to find other density altitude relations such as throttle stop, jetting, and blower overdrive.

What is claimed is:

1. A portable self-contained moistureless density altitude measuring apparatus comprising in combination: a housing; temperature sensing means in said housing and providing a temperature output; pressure sensing means in said housing and providing a pressure output; humidity sensing means in said housing and providing a humidity output; a microprocessor contained within said housing and having inputs connected with at least said temperature sensing means, said pressure sensing means, and said humidity sensing means for sampling the temperature outputs, pressure outputs and humidity outputs and calculating a moistureless gas density; said microprocessor also comprising a means for subtracting a moisture content in computing a moistureless gas density; and said microprocessor including means for outputting a moistureless density altitude derived from said moistureless gas density to said means for outputting a moistureless density altitude.

2. A moistureless density altitude measuring apparatus as defined in claim 1 wherein said means for outputting a moistureless density altitude is a liquid crystal display.

3. A moistureless density altitude measuring apparatus as defined in claim 1 wherein said means for outputting a moistureless density altitude includes a port for a printer.

4. A moistureless density altitude measuring apparatus as defined in claim 1 wherein said means for outputting a moistureless density altitude includes a disk drive.

5. A moistureless density altitude measuring apparatus as defined in claim 1 wherein said means for outputting a moistureless density altitude displays sequentially in predetermined time intervals of predetermined duration values of temperature, pressure, humidity and moistureless density altitude as calculated by said microprocessor.

6. A moistureless density altitude measuring apparatus as defined in claim 1 wherein said temperature sensing means is a thermistor.

7. A moistureless density altitude measuring apparatus as defined in claim 1 wherein said humidity sensing means is a capacitor.

8. A moistureless density altitude measuring apparatus as defined in claim 1 wherein said microprocessor also receives inputs from a keyboard.

\* \* \* \* \*